(12) United States Patent
Allmendinger

(10) Patent No.: US 8,737,701 B2
(45) Date of Patent: May 27, 2014

(54) CT IMAGE RECONSTRUCTION OF A MOVING EXAMINATION OBJECT

(75) Inventor: Thomas Allmendinger, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 1038 days.

(21) Appl. No.: 12/785,528

(22) Filed: May 24, 2010

(65) Prior Publication Data
US 2010/0303326 A1    Dec. 2, 2010

(30) Foreign Application Priority Data
May 26, 2009   (DE) .................. 10 2009 022 679

(51) Int. Cl.
G06K 9/00         (2006.01)

(52) U.S. Cl.
USPC ................................. 382/128; 378/8; 378/210

(58) Field of Classification Search
USPC ....................................... 382/128; 378/8, 210
See application file for complete search history.

(56) References Cited

U.S. PATENT DOCUMENTS

| | | | |
|---|---|---|---|
| 7,187,745 B2 | 3/2007 | Flohr | |
| 2003/0072419 A1* | 4/2003 | Bruder et al. | 378/210 |
| 2004/0120450 A1 | 6/2004 | Flohr | |
| 2005/0111622 A1* | 5/2005 | Bruder et al. | 378/95 |
| 2007/0053482 A1* | 3/2007 | Kohler et al. | 378/8 |
| 2007/0146325 A1* | 6/2007 | Poston et al. | 345/163 |
| 2008/0219527 A1 | 9/2008 | Lavi | |

FOREIGN PATENT DOCUMENTS

| | | |
|---|---|---|
| DE | 10245943 A1 | 4/2004 |
| DE | 102007029731 A1 | 1/2009 |

* cited by examiner

*Primary Examiner* — Luke Gilligan (74) *Attorney, Agent, or Firm* — Harness, Dickey & Pierce (57) ABSTRACT

A method is disclosed for reconstructing image data of a moving examination object from measured data, the measured data having been acquired during a rotating movement of a radiation source of a computed tomography system around the examination object. In at least one embodiment, first image data are determined from the measured data. Movement information is determined from the first image data by forming the difference between images. Time instants of little movement of the examination object are determined from the movement information, the determined time instants being dependent on the location or site within the examination object. Finally, second image data are reconstructed taking the determined time instants into account. These data can be output as result images.

18 Claims, 6 Drawing Sheets

CT IMAGE RECONSTRUCTION OF A MOVING EXAMINATION OBJECT

PRIORITY STATEMENT

The present application hereby claims priority under 35 U.S.C. §119 on German patent application number DE 10 2009 022 679.6 filed May 26, 2009, the entire contents of which are hereby incorporated herein by reference.

FIELD

At least one embodiment of the invention generally relates to a method for reconstructing image data of a moving examination object from measured data, the measured data having being acquired during a rotating movement of a radiation source of a computed tomography system around the examination object.

BACKGROUND

Methods for scanning an examination object by way of a CT system are generally known. In this case circular scans, sequential circular scans with advance, or spiral scans are used, for example. With the scans, absorption data of the examination object are recorded from different recording angles with the aid of at least one X-ray source and at least one oppositely disposed detector, and the thus collected absorption data or projections are computed by means of appropriate reconstruction methods into sectional images (slices) through the examination object.

A method referred to as filtered back-projection (FBP) is currently employed as the standard method for reconstructing computed tomography images from X-ray CT data sets of a computed tomography device (CT scanner), i.e. from the acquired projections. Following the data acquisition a step referred to as "rebinning" is performed in which the data generated by the beam widening out in the shape of fan from the source are re-ordered in such a way that they are present in a form as though the detector were struck by X-rays converging in parallel onto the detector. The data are then transformed into the frequency domain. Filtering takes place in the frequency domain and subsequently the filtered data are back-transformed. With the aid of the thus re-sorted and filtered data a back-projection is then performed onto the individual voxels within the volume of interest.

A disadvantage of these generally known calculation methods is that in the case of a moved or moving examination object, or an at least partially moved examination object, motion unsharpness can occur in the image, since during the time of a scanning operation to capture the data required for an image a displacement of the examination object or a part of the examination object can be present, with the result that not all the data that lead to an image reflect a spatially identical situation of the examination object. This motion unsharpness problem arises in a particularly extreme form during the performance of cardio CT examinations of a patient in which a strong motion unsharpness can occur in the cardiac region due to the cardiac movement or in the case of examinations in which relatively quick changes in the examination object are to be measured.

SUMMARY

In at least one embodiment of the invention, a method is disclosed for reconstructing CT images, wherein it is to be taken into account that the examination object moves. A corresponding control and computing unit, a CT system, a computer program and/or a computer program product are also disclosed in at least one embodiment.

According to at least one embodiment of the inventive method for reconstructing image data of a moving examination object from measured data, the measured data were acquired during a rotating movement of a radiation source of a computed tomography system around the examination object. First image data are determined from the measured data. Movement information is determined by forming the difference between images. Time instants of little movement of the examination object are determined from the movement information, the determined time instants being dependent on the location or site within the examination object. Second image data are reconstructed taking into account the determined time instants.

Since the examination object is a moving object, in particular a cyclically moving object such as e.g. a beating heart, it is advantageous for the image reconstruction to determine time instants at which the examination object is not moving or moving only slightly. The images of the examination object that are output as the result should then be reconstructed from data acquired at said time instants of little movement.

In order to enable suitable time instants of little movement to be determined, movement information of the examination object is ascertained first. This is obtained from differences between images reconstructed from the measured data. Reconstruction methods known per se can be called upon for the reconstruction of said first images. This applies equally to the second image data. The movement information obtained from the first image data serves as a basis for determining the time instants of little movement.

The determined time instants of little movement are not the same for the entire moving examination object. Rather, these differ from site to site. Thus, for example, a first time instant within a movement cycle of the examination object can be advantageous for the image reconstruction for a first sectional image (slice), while a different time instant within said movement cycle is better for a different slice.

In a development of at least one embodiment of the invention at least one function is defined which indicates a time instant of little, movement based on the site within the examination object. This function is therefore a space-related function with the aid of which it is possible to read off for which arbitrary site of the examination object a slight movement is present at which time instant. It is advantageous if two different functions are defined, each of which indicates a time instant of little movement as a function of the site within the examination object. The latter is suitable e.g. when two phases are present within a movement cycle of the examination object during which the examination object moves less than in the other phases.

It is advantageous if the at least one function or, as the case may be, the two functions represent spline functions. In this case the spline functions can have a plurality of sampling points that are equidistant in the space domain. Different types of constantly running functions are also possible.

In an embodiment of the invention, the at least one function or the two functions is/are calculated by minimizing a function containing the movement information. Minimization in relation to the movement information is advantageous, since time instants of little movement are searched for. Furthermore the function that is to be minimized can include a parameter for limiting the slope and/or a parameter for limiting the curvature of the at least one function that is to be calculated. These parameters enable specific properties of the function to be calculated within the scope of the minimization to be predefined. It is advantageous if time instants are varied for the purposes of the minimization. In this case the free parameters of the function used for the minimization are one or more time instants.

According to a development of at least one embodiment of the invention the first image data contain images of the entire examination object or, as the case may be, of the entire region of interest of the examination object for each time instant in a movement cycle of the examination object. In this case, therefore, the examination object moves cyclically, and the first image data enable a complete overview of which image is available at any given time instant within the movement cycle for any section of the examination object.

In an embodiment of the invention, the movement information indicates how strongly certain sites of the examination object move at certain time instants.

According to a development of at least one embodiment of the invention, the difference is formed between images which represent the same section of the examination object at different times within a movement cycle. The different times are preferably adjacent time instants. This type of difference forming can be performed for different sections of the examination object.

It is advantageous if the movement information forms a two-dimensional time- and space-dependent matrix. This means that a value for the movement information is present for each combination of time instant and site.

In an embodiment of the invention, the difference between images is formed by calculating individual differences between an individual image value of a first image and a corresponding individual image value of a second image in each case. Each of the images consists herein of a plurality of image values, the values of the different pixels of the image. In the forming of the difference, corresponding pixel values of two images are subtracted from one another in each case. The difference between the first and the second image is advantageously formed by summation of the individual differences.

In a development of at least one embodiment of the invention, parts of the measured data corresponding to the determined time instants are selected and used for reconstructing the second image data. The volume of measured data required for the reconstruction can be dependent on the reconstruction algorithm. The determined time instants indicate at least one data acquisition time which lies within said required volume of measured data.

The control and computing unit according to at least one embodiment of the invention serves for reconstructing image data of an examination object from measured data of a CT system. It includes a program memory for storing program code, there being present in said memory—possibly inter alia—program code that is suitable for performing a method of at least one embodiment of the above-described type. The CT system according to at least one embodiment of the invention includes such a control and computing unit. It can also contain other components which are required e.g. for acquiring measured data.

The computer program according to at least one embodiment of the invention has program code segments which are suitable for performing the method of the above-described type when the computer program is executed on a computer.

The computer program product according to at least one embodiment of the invention comprises program code segments which are stored on a computer-readable data medium and are suitable for performing the method of the above-described type when the computer program is executed on a computer.

BRIEF DESCRIPTION OF THE DRAWINGS

The invention is explained in more detail below with reference to an example embodiment and the accompanying figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
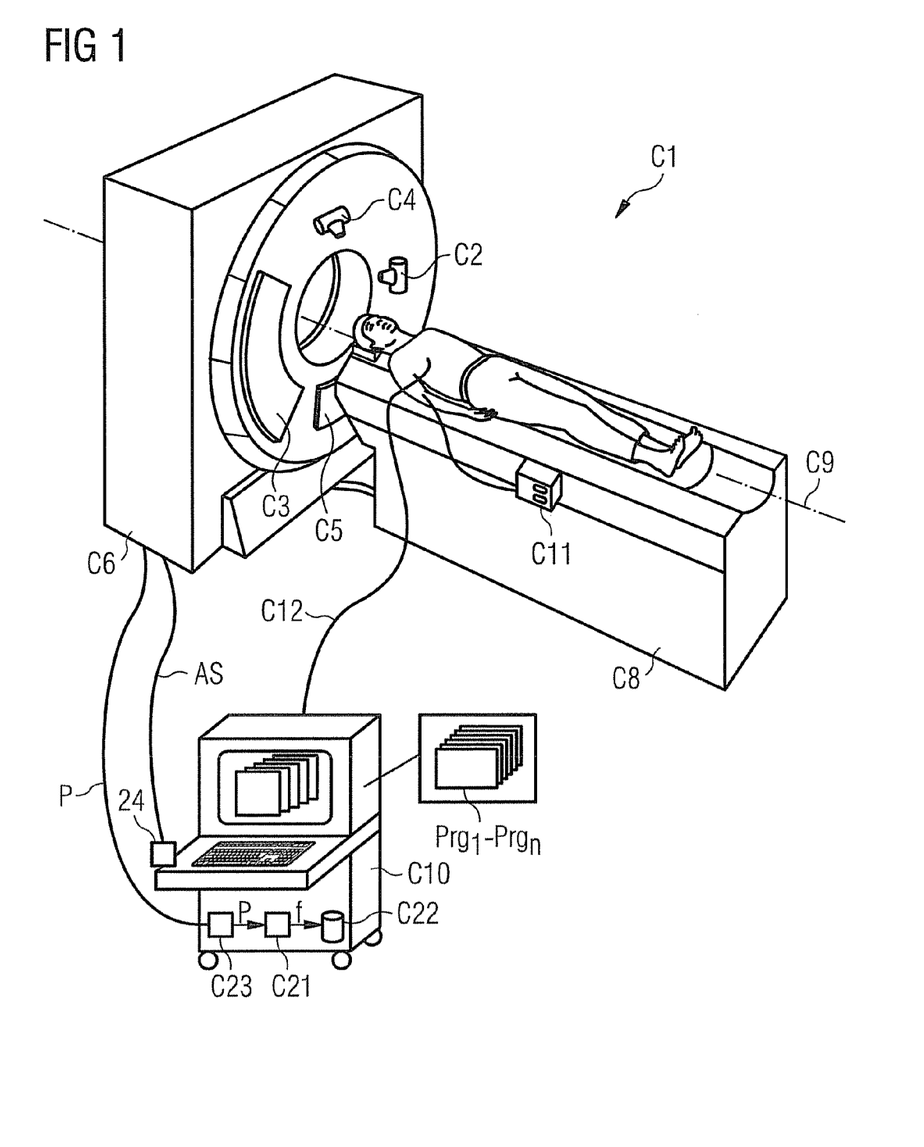
FIG. 1: shows a first schematic representation of an example embodiment of a computed tomography system having an image reconstruction component.

FIG. 1 firstly shows a schematic view of a first computed tomography system C1 having an image reconstruction device C21. Contained in the gantry housing C6 is a closed gantry (not shown here) on which a first X-ray tube C2 having an oppositely disposed detector C3 is arranged. Optionally, a second X-ray tube C4 having an oppositely disposed detector C5 is arranged in the CT system shown here, thereby enabling a higher time resolution to be achieved by virtue of the additionally available radiation source/detector combination, or, if different X-ray energy spectra are used in the radiation source/detector systems, also enabling "dual energy" examinations to be performed.

The CT system C1 additionally has a patient table C8 on which a patient can be moved during the examination along a system axis C9, also referred to as the z-axis, into the measurement field, wherein the scanning itself can take place both as a pure circular scan without patient advance exclusively in the examination region of interest. In this scenario the X-ray source C2 or C4 rotates around the patient in each case. In parallel therewith the detector C3 or C5 co-rotates with the X-ray source C2 or C4, respectively, in order to acquire projection measured data which are then used to reconstruct sectional images or slices. As an alternative to a sequential scan, in which the patient is moved incrementally through the examination field between the individual scans, it is of course also possible to perform a spiral scan, in which, in the course of the circumferential scanning by means of the X-ray radiation, the patient is moved continuously along the system axis C9 through the examination field between X-ray tube C2 or C4 and detector C3 or C5 respectively. With a spiral scan, the movement of the patient along the axis C9 and the simultaneous rotation of the X-ray source C2 or C4 cause the X-ray source C2 or C4 to follow a helical path relative to the patient during the measurement.

The CT system 10 is controlled by way of a control and computing unit C10 having computer program code $Prg_1$ to $Prg_n$ residing in a memory. Acquisition control signals AS can be transmitted from the control and computing unit C10 via a control interface 24 in order to control the CT system C1 in accordance with specific measurement protocols.

The projection measured data p (also referred to below as raw data) acquired by the detector C3 or C5 are passed to the control and computing unit C10 via a raw data interface C23. Following suitable preprocessing where appropriate, said raw data p are then processed further in an image reconstruction component C21. In the present example embodiment the image reconstruction component C21 is implemented in the control and computing unit C10 in the form of software on a processor, e.g. in the form of one or more of the computer program codes $Prg_1$ to $Prg_n$. The image data f reconstructed by the image reconstruction component C21 are then stored in a memory C22 of the control and computing unit C10 and/or output in the conventional manner on the monitor of the control and computing unit C10. The data can also be fed via an interface (not shown in FIG. 1) into a network connected to the computed tomography system C1, a radiological information system (RIS) for example, and stored in a mass storage device that is accessible there or output as images.

In addition the control and computing unit C10 can also perform the function of an ECG, a cable C12 being used between patient and control and computing unit C10 in order to derive the ECG potentials. In addition the CT system C1 shown in FIG. 1 also has a contrast agent injector C11 via which contrast agent can additionally be injected into the patient's bloodstream so that the vessels of the patient, in particular the ventricles of the beating heart, can be visualized more clearly. Furthermore this also affords the possibility of performing perfusion measurements, to which the proposed method is likewise suited.

Figure 2:
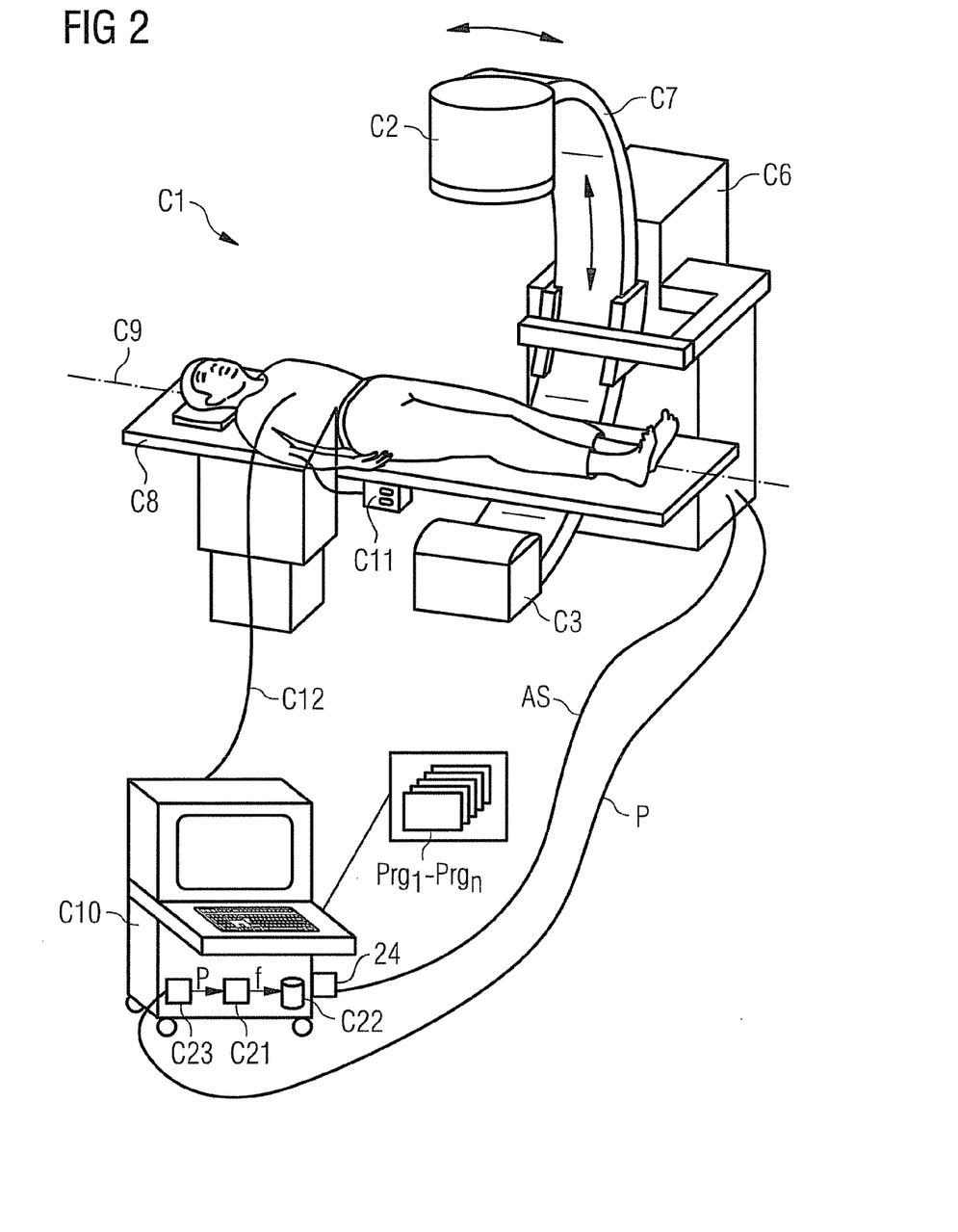
FIG. 2: shows a second schematic representation of an example embodiment of a computed tomography system having an image reconstruction component.

FIG. 2 shows a C-arm system in which, in contrast to the CT system shown in FIG. 1, the housing C6 carries the C arm C7 to which the X-ray tube C2 is secured on one side and the oppositely disposed detector C3 is secured on the other side. In order to perform a scan the C arm C7 is likewise pivoted around a system axis C9 so that scanning can take place from a plurality of scanning angles and corresponding projection data p can be determined from a plurality of projection angles. The C-arm system C1 of FIG. 2, like the CT system from FIG. 1, has a control and computing unit C10 of the type described with reference to FIG. 1.

Embodiments of the invention can be applied in both of the systems shown in FIGS. 1 and 2. Furthermore it can also be used in principle for other CT systems, e.g. for CT systems having a detector forming a complete ring.

Insofar as recordings are to be made of parts of the patient's body which do not move or can be immobilized, no significant problems pose themselves for the recording of the projections. A critical factor, in contrast, is the recording of projections of a cyclically or periodically moving object. An example of an examination object of said kind is the human heart. It is well known that the human heart essentially performs a periodic movement. In this case the periodic movement includes an alternating sequence of a rest or relaxation phase and a movement or beating phase. The rest phase typically lasts between 500 and 800 ms, and the beating phase lasts from 200 to 250 ms.

Figure 3:
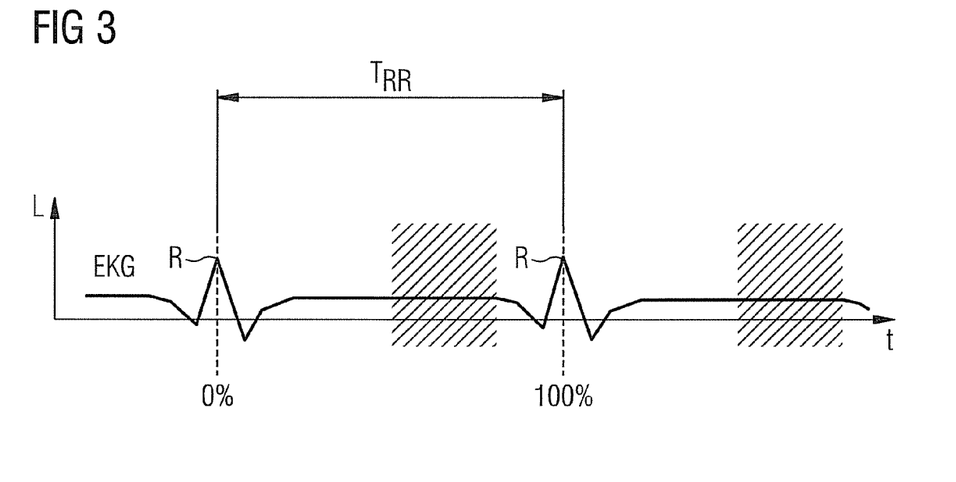
FIG. 3: shows a cardiac cycle.

This is apparent from FIG. 3, in which the level L of a patient's ECG signal designated by EKG is plotted over time t. The ECG signal illustrates the periodic movement of the patient's heart, the start of a cardiac cycle in each case being defined by an R wave R and the duration of the respective cardiac cycle by the RR interval TRR, i.e. the distance of the R wave R introducing the respective cardiac cycle from the R wave R introducing the following cardiac cycle. A cardiac phase starts at an R wave R at 0% and ends at the next R wave R at 100%. A conversion between the time dimension and the cardiac phase is possible at any time; for this purpose the ECG data can be used, from which data it is possible to derive at any given time instant which cardiac phase is currently present. A rest phase of the heart that is particularly favorable for reconstructing CT images, i.e. a phase of minimal heart movement, is indicated by hatching in each case.

In cardiac imaging by way of CT, the cardiac phase during which the data used for the image reconstruction are recorded is crucial for good image quality. For the image reconstruction an attempt is made to use data acquired during a cardiac phase with little or minimal cardiac movement. It is therefore necessary to decide which cardiac phase is particularly suitable for this. For that purpose data are recorded for all cardiac phases and for the entire range of the z-axis over which the heart or the part of the heart that is to be recorded extends. This can be accomplished by means of a series of sequential recordings or by means of a low-pitch spiral scan. The pitch is a dimensionless variable which corresponds to the ratio of patient table advance per rotation to the width of the detector, i.e. to the summed width across all detector rows in the case of a multi-row detector.

Sectional images (slices) of the heart are reconstructed from the acquired measured data. Following this first image reconstruction the result obtained is a matrix of images $I(p,z)$, where p stands for the cardiac phase or time of the data acquisition and z for the z position of the image, i.e. for a specific site within the heart or a specific axial section through the heart. Thus, images are available for all cardiac phases p and all z positions z. Said matrix $I(p,z)$ is used subsequently in order to identify favorable cardiac phases which are characterized by the smallest possible cardiac movement.

For each z position, the difference values of the images of this z position are formed. This takes place as follows:

The difference value referred to the images of the same z position and adjacent phase pn−1 and pn+1 is determined for each image $I(pn,z)$ of the phase pn. For that purpose the difference between the image and its one adjacent image of the phase pn−1 is determined by first subtracting each pixel value of the image of the phase pn from the corresponding pixel value of the adjacent image of the phase pn−1, and next calculating the sum of the absolute differences of all the image pixels. Finally the result is divided by the number of image pixels. This is also carried out for the other adjacent image of the phase pn+1, with the result that a difference value of the image of the phase pn relative to the adjacent image of the phase pn+1, and a difference value of the image of the phase pn relative to the adjacent image of the phase pn−1 are present. These two difference values relative to the two adjacent images are added and the result forms the difference value of the image of the phase pn. For a specific z position a difference value of this kind is determined for each phase value pn.

Alternatively hereto it is also possible for the difference value of the image of the phase pn to be determined solely in relation to one of its two neighbors, the same neighbor, i.e. either the neighbor with the smaller or the neighbor with the larger phase, being used for each image.

The difference values are determined for all z positions. The result obtained is a two-dimensional motion matrix $D(p,z)$ of difference values D, where p stands for the cardiac phase or time of the data recording and z for the z position of the image, i.e. for a specific axial section through the heart. The motion matrix $D(p,z)$ is therefore a two-dimensional matrix which represents a measure for the cardiac movement as a function of the phase p and the image position z. A motion matrix D of this kind is shown by way of example in FIG. 4A. In this case the z position z is plotted in mm on the abscissa and the time phase is plotted in % advancing downward on the ordinate. The motion matrix D contains precisely one heartbeat, i.e. a full movement cycle. Each grayscale value corresponds to a specific difference value in the range between 0.5 and 5.5. Bright areas indicate which cardiac regions exhibit little movement at which time instant or, as the case may be, at which cardiac phase. Conversely, cardiac regions and times of strong cardiac movement can be read off at dark areas. As already mentioned, a conversion between the time and the cardiac phase is possible at any time using the ECG information recorded during the CT data acquisition.

Figure 4A:
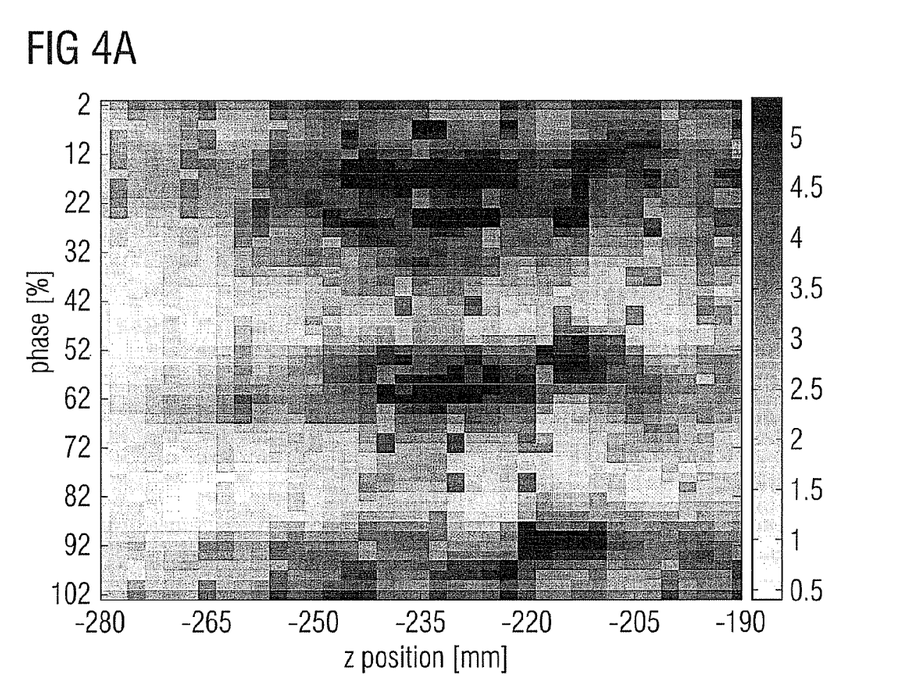
FIG. 4A: shows a motion matrix.

The liver of the recorded patient is located at the left-hand edge of the CT image shown in FIG. 4A. Proceeding toward the right, this is followed by the heart, the apex cordis being arranged on the left and the basis cordis on the right. It can be seen that two cardiac phases of little movement exist which can be read off at the two bright horizontal areas in the cardiac region within the motion matrix $D(p,z)$. The upper area is the systole, and the lower area the diastole. These areas are therefore particularly suitable for reconstructing images.

It would now be possible to determine those cardiac phases which—considered over the entire heart—correspond to a minimum of cardiac movement by looking at straight lines parallel to the x-axis and adding the difference values D along each straight line. The y value of the straight line having the smallest resulting summation value of the difference values would correspond to the cardiac phase having the smallest cardiac movement. Following this it would be possible to make available as the result of the imaging examination of the heart those images which correspond to this favorable cardiac phase. The basic limitation of this approach is that a single global best phase, i.e. applying to the entire heart, is calculated. It is, however, possible that different local best cardiac phases having minimal movement exist for different regions of the heart. For example, it could be more favorable to reconstruct the apex cordis at a phase of 70% and the basis cordis at a phase of 75%.

Figure 4B:
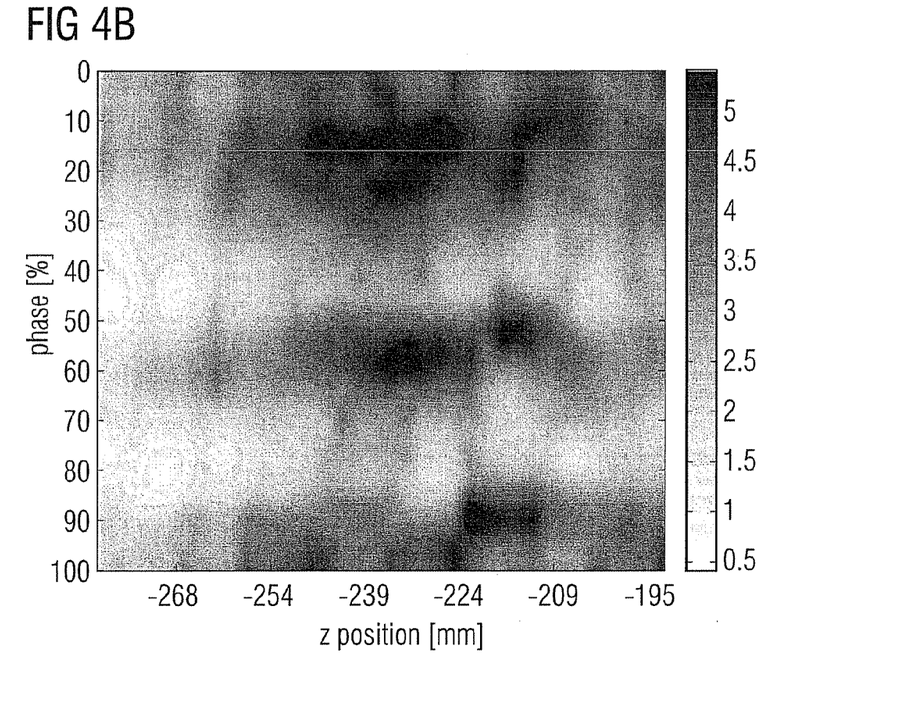
FIG. 4B: shows a revised motion matrix.

In the following it is revealed how it is possible to take local best cardiac phases into account for the image reconstruction. Toward that end the motion matrix $D(p,z)$ of FIG. 4A is first transferred by way of filtering and interpolation onto a more finely resolved two-dimensional grid. The motion matrix $D(p,z)$ of FIG. 4A has a typical size of 50×50 matrix dots. This corresponds to 50 sampling points for the cardiac phase from 0% to 100% in 2% increments, and 50 increments in the z direction which cover the volume of the heart in increments of approx. 2 mm. Assuming a pulse rate of 60 beats per minute, the spacing in the phase direction amounts to 20 ms. As already mentioned, this absolute phase consideration is equivalent to the relative one. The motion matrix $D(p,z)$ of FIG. 4A is now smoothed in the phase direction and z direction with the aid of a Gaussian filter, e.g. of width 2, in order to eliminate local outliers in the values. Following this, the matrix is brought to a finer grid by linear interpolation of the sampling points such that the grid is increased in size to approx. 500 dots both in the phase direction and in the z direction. This modified motion matrix D(p,z) is shown in FIG. 4B. The representation of FIG. 4A therefore shows the original motion matrix D(p,z) obtained from the measured data, and FIG. 4B shows the motion matrix D(p,z) obtained herefrom by smoothing and interpolation. The matrix shown in FIG. 4B is a quasi-smooth function which is suitable for the minimization procedure that is described below.

Figure 5:
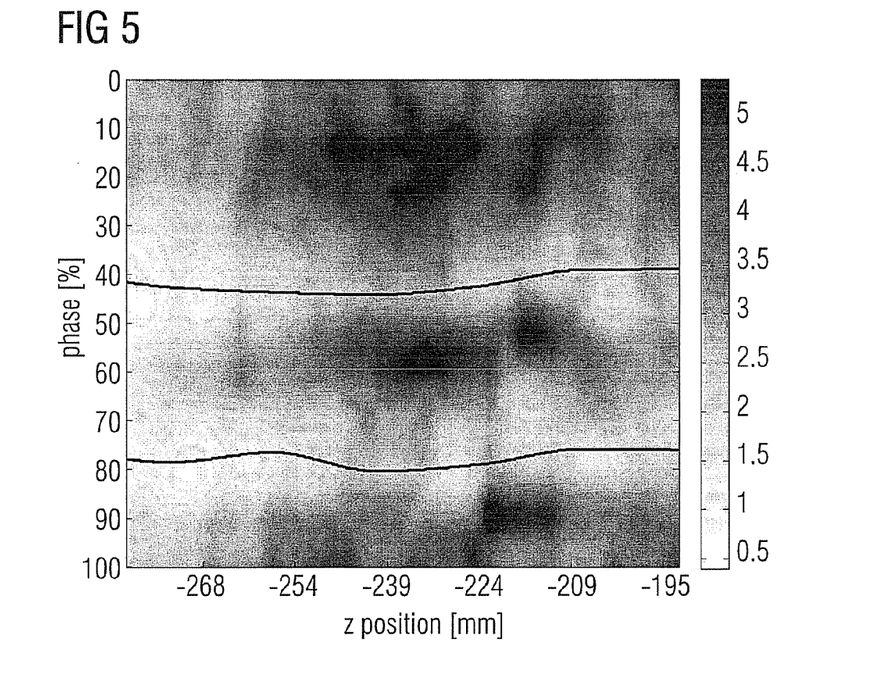
FIG. 5: shows a motion matrix having two curves which indicate an optimal cardiac phase.

Two continuous functions $f_S(X_k,z)$ and $f_D(X_k,z)$ are now defined with the aid of a minimization procedure. The index S and D of the functions indicates a section of the cardiac phase, where S stands for systole and D for diastole. The functions $f_S(X_k,z)$ and $f_D(X_k,z)$ are intended to indicate the optimal shape of the cardiac phase to be used for the image reconstruction for the systolic and the diastolic section of the cardiac phase over the z variable. Thus, if a specific position z of the heart is inserted into the functions $f_S(X_k,z)$ and $f_D(X_k,z)$, the best cardiac phase within the systole or diastole for this site is obtained by application of the respective function. Functions of this kind are shown in FIG. 5, wherein they have been entered into the motion matrix D(p,z) of FIG. 4B. The upper bright curve shows the function $f_S(X_k,z)$ for the systole and the lower dark curve the function $f_D(X_k,z)$ for the diastole.

The functions $f_S(X_k,z)$ and $f_D(X_k,z)$ have seven sampling points $X_k$ in the z direction; thus, $X_k$ relates to specific z values specified at the start of the calculation. These values are uniformly distributed over the scan range present, i.e. the extension range of the abscissa of FIG. 4B. Other values can, of course, also be used for the number of sampling points. It is favorable if the distance between two sampling points $X_k$ equals approx. 2 cm.

The phase values associated with the sampling points $X_k$ are denoted by $PS_k$ for the systolic curve and by $PD_k$ for the diastolic curve. Interpolated between these values, both for the systole and for the diastole is a piecewise cubic hermitian polynomial which continuously continues the function and its derivative at the sampling points. These functions—corresponding to the functions $f_S(X_k,z)$ and $f_D(X_k,z)$—are splines. A spline of n-th degree is a function composed piecewise of polynomials having maximum degree n. Certain conditions are set at the z positions at which two polynomial pieces collide, for example that the spline can be constantly differentiated (n-1) times.

If the phase values $PS_k$ and $PD_k$ have been specified for the systole and the diastole of the sampling points $X_k$, then the functions $f_S(X_k,z)$ and $f_D(X_k,z)$ are defined automatically via the spline interpolation between said sampling points. It is therefore expedient to determine the phase values $PS_k$ and $PD_k$ of the sampling points $X_k$. This is accomplished by way of a minimization calculation. To that end the following function is minimized:

$$E(X_k) = \sum_z (D(f_s(X_k, z), z)^2 + D(f_D(X_k, z), z)^2)$$

In this case D(f,z) is the value of the motion matrix of FIG. 4B at the phase f and the heart position z. The function E that is to be minimized therefore contains the values of the motion matrix D(f,z), summed along the shape of the functions $f_S(X_k,z)$ and $f_D(X_k,z)$. Since it is desired to determine cardiac phases with minimum cardiac movement, E should therefore be as small as possible.

The phase values $PS_k$ and $PD_k$ of the sampling points $X_k$ these correspond to the values of the functions $f_S(X_k,z)$ and $f_D(X_k,z)$ if the positions of the sampling points $X_k$ are entered for z—are the free parameters of the function E. These are varied for the purpose of minimizing E. Owing to such a minimization of E the phase values $PS_k$ and $PD_k$ of the sampling points $X_k$ are obtained as the result, and consequently by spline interpolation the shape of the functions $f_S(X_k,z)$ and $f_D(X_k,z)$.

The function E that is to be minimized contains both the systolic and the diastolic values. A common optimization of the two curves therefore takes place. In a departure herefrom it is also possible to use a function that is to be minimized individually for the diastolic function $f_D(X_k,z)$ and the systolic function $f_S(X_k,z)$.

Furthermore it was assumed in the prior art that the sampling points $X_k$ for the two functions $f_S(X_k,z)$ and $f_D(X_k,z)$ are located at the same z positions. Alternatively hereto these can of course be different from one another without the need to deviate from the approach described for the rest.

It is advantageous if use is made of auxiliary functions C1, C2 and C3 which limit the freedom of the minimization process and so stabilize the fit:

$$C1 = \max\left(\left(\sum_k \left(\frac{PS_{k+1}-}{PS_k}\right)^2\right)-\right)^4 + \max\left(\left(\sum_k \left(\frac{PD_{k+1}-}{PD_k}\right)^2\right)-\right)^4$$
$$T1; 0 \qquad\qquad T1; 0$$

$$C2 = \max\left(\left(\sum_k \frac{\left(\frac{PS_{k+2}-}{PS_{k+1}}\right)^2-}{(PS_{k+1}-PS_k)^2}\right)-\right)^4 + \max\left(\left(\sum_k \frac{\left(\frac{PD_{k+2}-}{PD_{k+1}}\right)^2-}{(PD_{k+1}-PD_k)^2}\right)-\right)^4$$
$$T2; 0 \qquad\qquad T2; 0$$

$$C3 = \max\left(\left(\sum_k PD_k - PS_k\right) - T3; 0\right)^4$$

The maximum function max(a;b) outputs the greater of the two values a and b as its result.

In this case C1 serves to limit the slope of the phase values between adjacent sampling points, and C2 serves to limit the curvature of the curves. The intended effect of C3 is that the diastolic curve will always lie at a later phase than the systolic curve. The three settable parameters T1, T2 and T3 are used to control the weighting. The function to be minimized is now yielded using the auxiliary functions C1, C2 and C3:

$$E(X_k) = \sum_z (D(f_s(X_k, z), z)^2 + D(f_D(X_k, z), z)^2) + C1 + C2 + C3.$$

Figure 6:
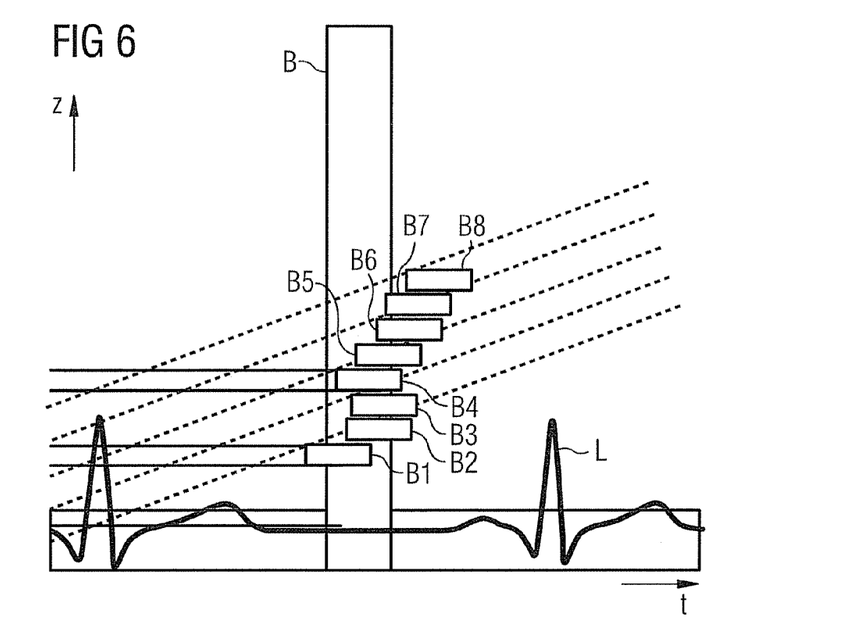
FIG. 6: schematically shows data used for the image reconstruction.

Following the determination of the functions $f_S(X_k,z)$ and $f_D(X_k,z)$, the reconstruction of the images now takes place image by image, based on an image reconstruction algorithm known per se. This is illustrated in FIG. 6. In order to simplify the illustration, FIG. 6 shows the image reconstruction only for the diasystolic, not for the systolic section. Typically, the entire heart volume is reconstructed by means of layer images having a thickness of 0.6 mm with an increment of 0.5 mm between the images.

The shape of the time t is plotted toward the right. As in FIG. 3, the level L of the ECG signal is plotted in the lower part of FIG. 6. The ordinate shows the z position; this corresponds to the patient table position in the course of the CT scan. The dotted lines show the course of the detector position in the case of a spiral scan having a pitch of approximately 0.2. The entire area between the two outer dotted lines is therefore the area for which data are available for the image reconstruction. Within said area images of the heart can now be reconstructed in a cardiac-phase-correlated manner based on the knowledge of the function $f_S(X_k,z)$.

The bar B indicates in this case how images would be reconstructed if a single cardiac phase were to be regarded as optimal for the entire heart and used for the reconstruction. In this case, therefore, the data of the time segment marked by the bar B would be used for the reconstruction for the layer image of each z position.

In contrast hereto, the data of the different time segments according to the bars B1 to B8 are now used for the image reconstruction for the different layer images. The position of the bars B1 to B8 is shifted slightly relative to one another in time t. This corresponds to the shape of the function $f_S(X_k,z)$, since different cardiac phases were determined as suitable for the image reconstruction for different cardiac regions with the aid of said function. For each individual image which is to be reconstructed at a specific z position, use is therefore made of precisely the data corresponding to the previously determined optimal phase at said z position. In this way the entire heart volume is reconstructed image by image, the phase being varied accordingly.

Analogously to the approach explained for the diastole, images of the entire heart volume are also reconstructed for the systolic section.

Figure 7A:
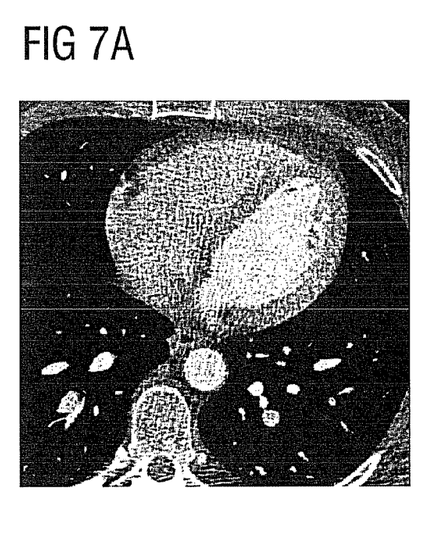
FIG. 7: shows four CT images.
Figure 7B:
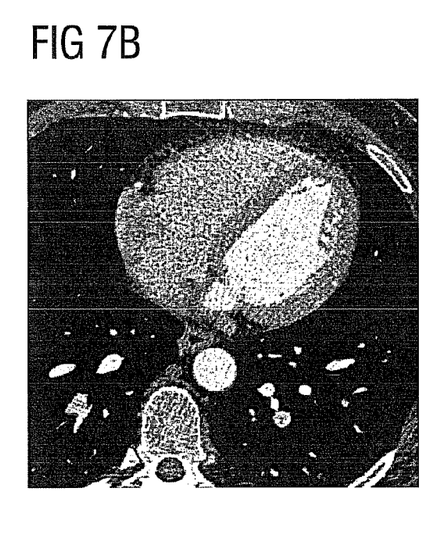

FIGS. 7A to 7D shows CT images which have been reconstructed as described above. FIGS. 7A and 7B show a slice through the heart at the level of the mid-segment of the right coronary artery, a constant best cardiac phase for the entire heart volume having been assumed for the reconstruction of the image of FIG. 7A, whereas an approach involving dynamic phase reconstruction, i.e. using the functions $f_S(X_k,z)$ and $f_D(X_k,z)$, was adopted for the reconstruction of the image of FIG. 7B. Motion artifacts are clearly visible in FIG. 7A, whereas the quality of the image of FIG. 7B is visibly superior. In this regard let the right coronary artery in image 7B be considered (this can be seen as a clear white spot, approx. 3-4 mm in diameter, in the top left-hand region of the heart). FIG. 7B provides a very clear representation of the right coronary artery. The comparable point of the image shown in FIG. 7A is unsharp and faded.

Figure 7C:
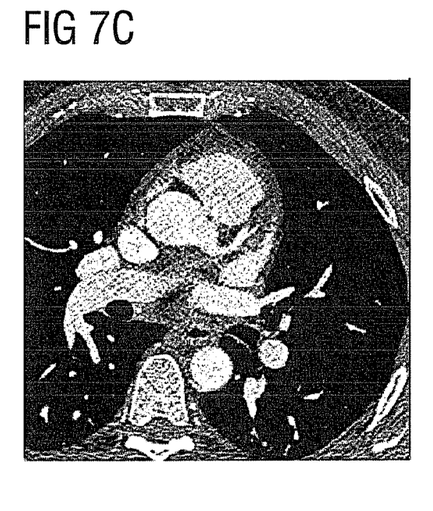
Figure 7D:
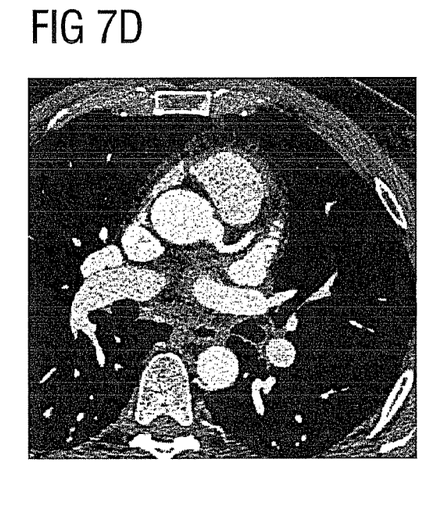

The same applies also to FIGS. 7C and 7D: these figures show a slice through the upper region of the heart at the level of the left main coronary artery, a constant best cardiac phase for the entire heart volume having been assumed for the reconstruction of the image of FIG. 7C, whereas a dynamic phase reconstruction approach was used for the reconstruction of the image of FIG. 7D. Motion artifacts are clearly visible in FIG. 7C, whereas the quality of the image of FIG. 7D is visibly superior. The better image of FIG. 7D shows an approximately 2-3 cm long and 5 mm thick arterial region in the middle of the heart near to the round white elements. In the image illustrated in FIG. 7C the same point shows a clear dual structure which has been produced due to movement.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention has been described in the foregoing with reference to an exemplary embodiment. It is understood that numerous changes and modifications are possible without leaving the scope of the invention.

What is claimed is:

1. A method for reconstructing image data of a moving examination object from measured data, the measured data being acquired during a rotating movement of a radiation source of a computed tomography system around the examination object, the method comprising:
   determining, by a computer, first image data from the measured data;
   determining movement information by forming a difference between images from the determined first image data;
   determining at least,
      a first time instant, using at least a first continuous function or a second continuous function, of relatively little movement of a first site within the examination object from the determined movement information, and
      a second time instant, using one of the at least a first continuous function and a second continuous function used in determining the first time instant, of relatively little movement of a second site within the examination object from the determined movement information; and
   reconstructing second image data, using the measured data corresponding to the determined at least first and second time instants, wherein each of the first and second situ corresponds to a specific axial section through the examination object.

2. The method as claimed in claim 1, wherein the first and second continuous functions are spline functions.

3. The method as claimed in claim 2, wherein each of the spline functions has a plurality of sampling points that are equidistant in the space domain.

4. The method as claimed in claim 1, wherein each of the first and second continuous functions is calculated by minimizing a function containing the movement information.

5. The method as claimed in claim 4, wherein the function that is to be minimized contains at least one of a parameter for limiting the slope and a parameter for limiting the curvature of the at least one function that is to be calculated.

6. The method as claimed in claim 4, wherein the first and second time instants are varied for the purposes of the minimization.

7. The method as claimed in claim 1, wherein the first image data contain images of the entire examination object for each time instant of a movement cycle of the examination object.

8. The method as claimed in claim 1, wherein the movement information indicates how strongly specific sites of the examination object move at specific time instants within a movement cycle of the examination object.

9. The method as claimed in claim 1, wherein the difference is formed between images which represent the same section of the examination object at different times within a movement cycle of the examination object.

10. The method as claimed in claim 9, wherein the difference is formed for different sections of the examination object.

11. The method as claimed in claim 1, wherein the movement information forms a two-dimensional time- and space-dependent matrix.

12. The method as claimed in claim 1, wherein the difference between images is formed by calculating individual differences between an individual image value of a first image and a corresponding individual image value of a second image in each case.

13. The method as claimed in claim 12, wherein the difference between the first and the second image is formed by summing the individual differences.

14. The method as claimed in claim 1, wherein parts of the measured data corresponding to the determined time instants are selected and used for reconstructing the second image data.

15. A computer tomography (CT) system comprising:
   a control and computing unit configured to,
      determine first image data from measured data, the measured data being acquired during a rotating movement of a radiation source of the CT system around a moving examination object;
      determine movement information by forming a difference between images from the determined first image data;
      determine at least,
         a first time instant, using at least a first continuous function or a second continuous function, of relatively little movement of a first site within the examination object from the determined movement information, and
         a second time instant, using one of the at least a first continuous function and a second continuous function used in determining the first time instant, of relatively little movement of a second site within the examination object from the determined movement information; and
      reconstruct second image data, using the measured data corresponding to the determined at least first and second time instants, wherein each of the first and second sites corresponds to a specific axial section through the examination object.

16. A non-transitory computer readable medium including a computer program product, the computer program product comprising program code segments, which when executed by a processor, causes the processor to perform functions including:
   determining first image data from measured data, the measured data being acquired during a rotating movement of a radiation source of the CT system around a moving examination object;
   determining movement information by forming a difference between images from the determined first image data;
   determining at least
      a first time instant, using at least a first continuous function or a second continuous function, of relatively little movement of a first site within the examination object from the determined movement information, and
      a second time instant, using one of the at least a first continuous function and a second continuous function used in determining the first time instant, of relatively little movement of a second site within the examination object from the determined movement information; and reconstructing second image data, using the measured data corresponding to the determined at least first and second time instants, wherein each of the first and second sites corresponds to a specific axial section through the examination object.

17. The method as claimed in claim 16, wherein each of the first and second continuous functions represents a spline function.

18. The method as claimed in claim 17, wherein each of the spline functions has a plurality of sampling points that are equidistant in the space domain.

* * * * *